US011076993B2

(12) United States Patent
Campos et al.

(10) Patent No.: US 11,076,993 B2
(45) Date of Patent: *Aug. 3, 2021

(54) VACUUM LOSS DETECTION DURING LASER EYE SURGERY

(71) Applicant: AMO DEVELOPMENT, LLC, Santa Ana, CA (US)

(72) Inventors: Michael A. Campos, Fremont, CA (US); Javier G. Gonzalez, Palo Alto, CA (US); Teresa G. Miller-Gadda, Palo Alto, CA (US)

(73) Assignee: AMO Development, LLC, Santa Ana, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 16/253,161

(22) Filed: Jan. 21, 2019

(65) Prior Publication Data

US 2019/0151145 A1 May 23, 2019

Related U.S. Application Data

(62) Division of application No. 14/885,907, filed on Oct. 16, 2015, now Pat. No. 10,195,085.

(Continued)

(51) Int. Cl.
*A61F 9/009* (2006.01)
*A61F 9/00* (2006.01)
*A61F 9/008* (2006.01)

(52) U.S. Cl.
CPC ........ *A61F 9/009* (2013.01); *A61B 2217/005* (2013.01); *A61F 2009/0052* (2013.01);

(Continued)

(58) Field of Classification Search
CPC .............. A61F 9/009; A61F 2009/0035; A61F 2009/0043; A61F 2009/0052;

(Continued)

(56) References Cited

U.S. PATENT DOCUMENTS 5,459,570 A   10/1995  Swanson et al.
5,720,894 A   2/1998   Neev et al.

(Continued)

FOREIGN PATENT DOCUMENTS

WO   2006090217 A1   8/2006

OTHER PUBLICATIONS

International Search Report and Written Opinion for Application No. PCT/US2015/056092, dated Jan. 26, 2016, 9 pages.

*Primary Examiner* — Ahmed M Farah
(74) *Attorney, Agent, or Firm* — Johnson & Johnson Surgical Vision, Inc.

(57) ABSTRACT

A laser eye surgery system that has a patient interface between the eye and the laser system relying on suction to hold the interface to the eye. The patient interface may be a liquid-filled interface, with liquid used as a transmission medium for the laser. During a laser procedure various inputs are monitored to detect a leak. The inputs may include a video feed of the eye looking for air bubbles in the liquid medium, the force sensors on the patient interface that detect patient movement, and vacuum sensors directly sensing the level of suction between the patient interface and the eye. The method may include combining three monitoring activities with a Bayesian algorithm that computes the probabilities of an imminent vacuum loss event.

10 Claims, 10 Drawing Sheets

Related U.S. Application Data

(60) Provisional application No. 62/065,481, filed on Oct. 17, 2014.

(52) U.S. Cl.
CPC ............... *A61F 2009/00844* (2013.01); *A61F 2009/00872* (2013.01); *A61F 2009/00878* (2013.01); *A61F 2009/00887* (2013.01)

(58) Field of Classification Search
CPC .. A61F 2009/00844; A61F 2009/00872; A61F 2009/00878; A61F 9/008; A61B 2217/00; A61B 2217/002; A61B 2217/005; A61B 2217/007
USPC ....................... 606/4–6, 10–13, 166; 128/898
See application file for complete search history.

(56) References Cited

U.S. PATENT DOCUMENTS

| | | | |
|---|---|---|---|
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A | 4/2000 | Wei et al. | |
| 6,111,645 A | 8/2000 | Tearney et al. | |
| 6,454,761 B1 | 9/2002 | Freedman | |
| 7,655,002 B2 | 2/2010 | Myers, I et al. | |
| 7,717,907 B2 | 5/2010 | Ruiz et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,394,084 B2 | 3/2013 | Blumenkranz et al. | |
| 8,414,564 B2 | 4/2013 | Goldshleger et al. | |
| 8,414,664 B2 | 4/2013 | Heilmann et al. | |
| 8,425,497 B2 | 4/2013 | Blumenkranz et al. | |
| 8,500,724 B2 | 8/2013 | Blumenkranz et al. | |
| 9,301,878 B2 * | 4/2016 | Raksi | A61F 9/009 |
| 9,987,165 B2 | 6/2018 | Gooding et al. | |
| 10,195,085 B2 * | 2/2019 | Campos | A61F 9/009 |
| 10,285,860 B2 * | 5/2019 | Gooding | A61M 1/0052 |
| 10,881,552 B2 * | 1/2021 | Rathjen | A61F 9/009 |
| 2011/0190739 A1 * | 8/2011 | Frey | A61F 9/009 606/4 |
| 2011/0319873 A1 * | 12/2011 | Raksi | A61F 9/009 606/1 |
| 2011/0319875 A1 * | 12/2011 | Loesel | A61F 9/00825 606/4 |
| 2014/0128821 A1 | 5/2014 | Gooding et al. | |
| 2014/0128852 A1 | 5/2014 | Gooding et al. | |
| 2014/0163534 A1 | 6/2014 | Angeley et al. | |
| 2014/0343541 A1 | 11/2014 | Scott et al. | |
| 2015/0018674 A1 | 1/2015 | Scott et al. | |
| 2015/0190278 A1 | 7/2015 | Gooding et al. | |
| 2016/0106581 A1 | 4/2016 | Gonzalez et al. | |
| 2016/0175146 A1 * | 6/2016 | Gooding | A61F 9/008 606/4 |
| 2016/0331231 A1 * | 11/2016 | Studer | A61F 9/009 |
| 2018/0000641 A1 * | 1/2018 | Rathjen | A61F 9/008 |

\* cited by examiner

VACUUM LOSS DETECTION DURING LASER EYE SURGERY

RELATED APPLICATION

This application is a divisional of and claims priority to U.S. patent application Ser. No. 14/885,907, filed Oct. 16, 2015, which is a non-provisional application and claims the benefit under 35 U.S.C. § 119(e) of U.S. Provisional Application Ser. No. 62/065,481, filed Oct. 17, 2014, all of which are incorporated herein in their entirety as if fully set forth.

FIELD OF THE INVENTION

The present application pertains to laser-assisted eye surgery using a vacuum-held optical interface and, more particularly, to systems and methods for monitoring and reacting to insufficient vacuum within the interface.

BACKGROUND

A cataract is formed by opacification of the crystalline lens or its envelope—the lens capsule—of the eye. The cataract obstructs passage of light through the lens. A cataract can vary in degree from slight to complete opacity. Early in the development of an age-related cataract, the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. If left untreated, cataracts may cause blindness.

A common cataract treatment involves replacing the opaque crystalline lens with an artificial intraocular lens (IOL). Every year, an estimated 15 million cataract surgeries are performed worldwide. Traditionally, cataract surgery has been typically performed using a technique called phacoemulsification in which an ultrasonic tip with associated irrigation and aspiration ports is used to sculpt the relatively hard nucleus of the lens to facilitate removal through an opening made in the anterior lens capsule. Access to the lens nucleus can be provided by performing an anterior capsulotomy in which a small round hole is formed in the anterior side of the lens capsule using a surgical. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

One of the most technically challenging and critical steps in the cataract extraction procedure is providing access to the lens nucleus for removal of the cataract by phacoemulsification. The desired outcome is to provide a smooth continuous circular opening through which phacoemulsification of the nucleus can be performed safely and easily, and also through which an intraocular lens may be easily inserted. Because of the criticality of this step, some surgeons prefer a surgical laser beam over manual tools like microkeratomes and forceps since the laser beam can be focused precisely on extremely small amounts of eye tissue, thereby enhancing the accuracy and reliability of the capsulotomy procedure.

Several commercial laser-assisted eye surgery systems are available to facilitate cataract removal and astigmatism correction. The CATALYS Precision Laser System from Abbott Medical Optics is indicated for anterior capsulotomy, phacofragmentation, and the creation of single plane and multi-plane arc cuts/incisions in the cornea to correct astigmatism. The CATALYS System uses a two-piece liquid-filled interface that docks with the patient's eye and provides a clear optical path for real-time video, OCT imaging, and laser treatment. Aspects of the CATALYS System are disclosed in U.S. Pat. Nos. 8,394,084, 8,500,724, 8,425,497, U.S. Patent Publication 2014/0163534, U.S. patent application Ser. No. 14/256,307, filed Apr. 18, 2014 (published as U.S. Patent Publication No. 2015/0018674 on Jan. 15, 2015), and U.S. patent application Ser. No. 14/255,430, filed Apr. 17, 2014 (published as U.S. Patent Publication No. 2014/0343541 on Nov. 20, 2014), the contents of all of which are incorporated herein by reference as if fully set forth. Other systems for laser cataract surgery are the LenSx Laser from Alcon Laboratories, Inc., the LENSAR Laser System from LENSAR, Inc., and the VICTUS Femtosecond Laser Platform from TECHNOLAS Perfect Vision GmbH a Bausch+Lomb Company.

One drawback with current systems is with the docking interfaces between the eye and the laser system. Most docking interfaces rely on suction to hold the interface to the eye, and sometimes to hold separate pieces of the interface together. If during a laser procedure the level of vacuum in any of these couplings diminishes, an adverse event may occur. In particular with liquid-filled interfaces, the liquid is used as a transmission medium for the laser, and a loss of vacuum may introduce air which has a different index of refraction than the liquid and would affect the laser optics. Although detecting a sudden and significant pressure differential signals an adverse condition, sometimes pressure fluctuations do not lead to failure. Stopping the laser in the middle of the surgery when it is not necessary is also undesirable. Furthermore, in some instances of a vacuum loss, the water displaced from the patient interface is aspirated by the vacuum system, decreasing the effectiveness with which the system detects a vacuum loss event. Accordingly, there is a need for sophisticated systems for detecting such loss of suction.

SUMMARY

Improved laser eye surgery systems, and related methods, are provided. The laser eye surgery systems use a laser to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye. An optical coherence tomography (OCT) scanning subsystem to measure the spatial disposition of external and internal structures of the eye in which incisions can be formed. The laser eye surgery system further includes an alignment subsystem, shared optics operable to scan the treatment beam, and an alignment subsystem relative to the laser eye surgery system. The alignment subsystem can include a video subsystem that can be used to, for example, provide images of the eye during docking of the eye to the laser eye surgery system. In a preferred embodiment, a liquid interface is used between a patient interface lens and the eye. The use of the liquid interface avoids imparting undesirable forces to the patient's eye.

A laser eye surgery system that has a patient interface between the eye and the laser system relying on suction to hold the interface to the eye. The patient interface may be a liquid-filled interface, with liquid used as a transmission medium for the laser. During a laser procedure various inputs are monitored to detect a leak. The inputs may include a video feed of the eye looking for air bubbles in the liquid medium, the force sensors on the patient interface that detect patient movement, and vacuum sensors directly sensing the level of suction between the patient interface and the eye. The method may include combining three monitoring activities with a Bayesian algorithm that computes the probabilities of an imminent vacuum loss event.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Methods and systems related to laser eye surgery are disclosed. A laser is used to form precise incisions in the cornea, in the lens capsule, and/or in the crystalline lens nucleus. In a preferred embodiment, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system and also provide images of the eye once the docking process is complete. In a preferred embodiment, a liquid interface is used between a patient interface lens and the eye. The use of the liquid interface avoids imparting undesirable forces to the patient's eye.

Laser System Configuration

Figure 1:
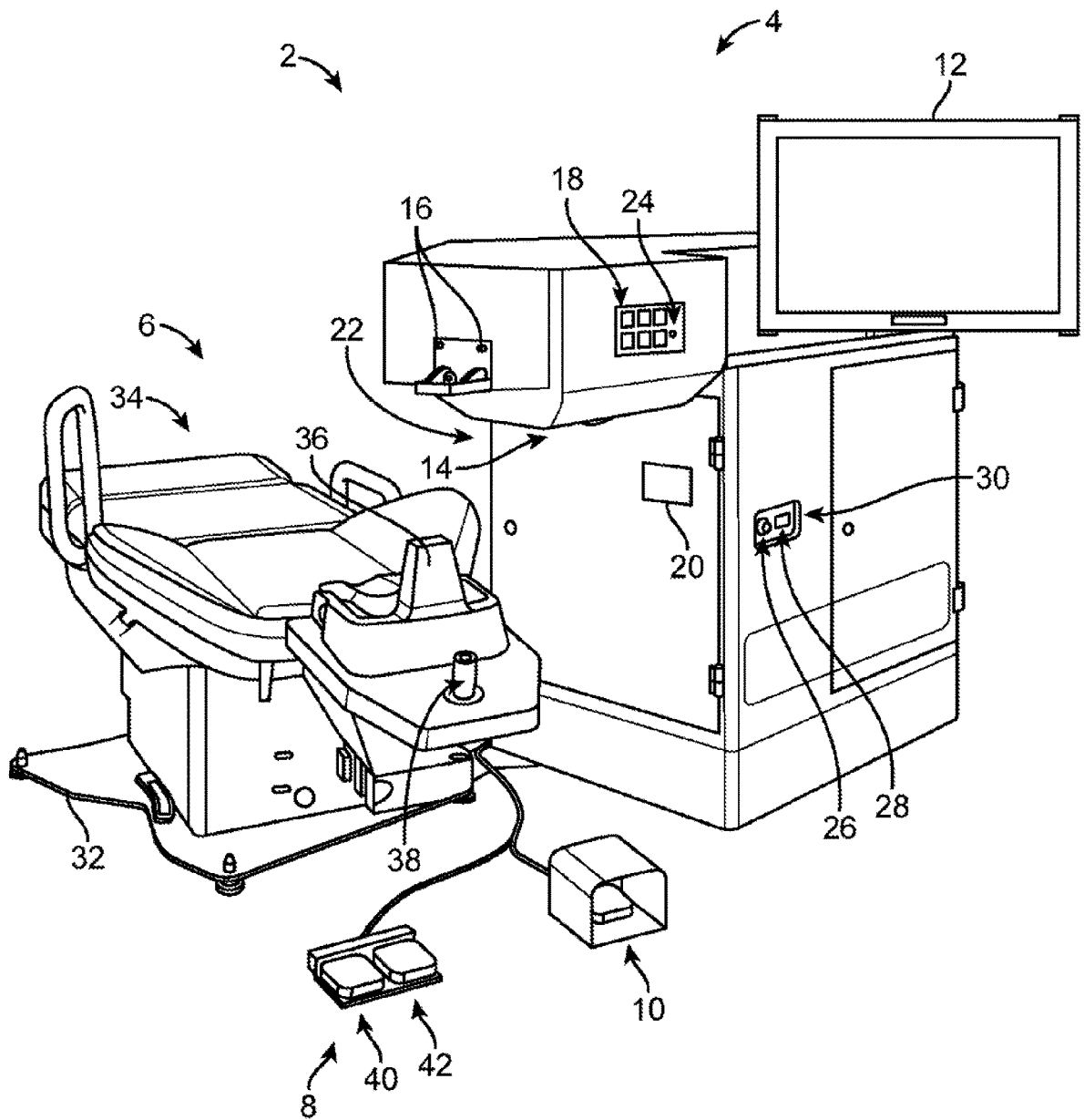
FIG. 1 is a perspective view showing a laser eye surgery system, in accordance with the present application.

FIG. 1 shows a laser eye surgery system 2, in accordance with the present application, operable to form precise incisions in the cornea, in the lens capsule, and/or in the crystalline lens nucleus. The system 2 includes a diagnostic and interventional unit 4, a patient chair 6, a dual function footswitch 8, and a laser footswitch 10.

The diagnostic and interventional unit 4 houses many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism (internal, not shown), and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the diagnostic and interventional unit 4 with the patient chair back in an upright position and patient footrest in a lowered position. In the suction ring capture position, the chair is rotated out from under the diagnostic and interventional unit 4 with the patient chair back in reclined position and patient footrest in raised position. In the patient treat position, the chair is rotated under the diagnostic and interventional unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In a preferred embodiment, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In a preferred embodiment, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
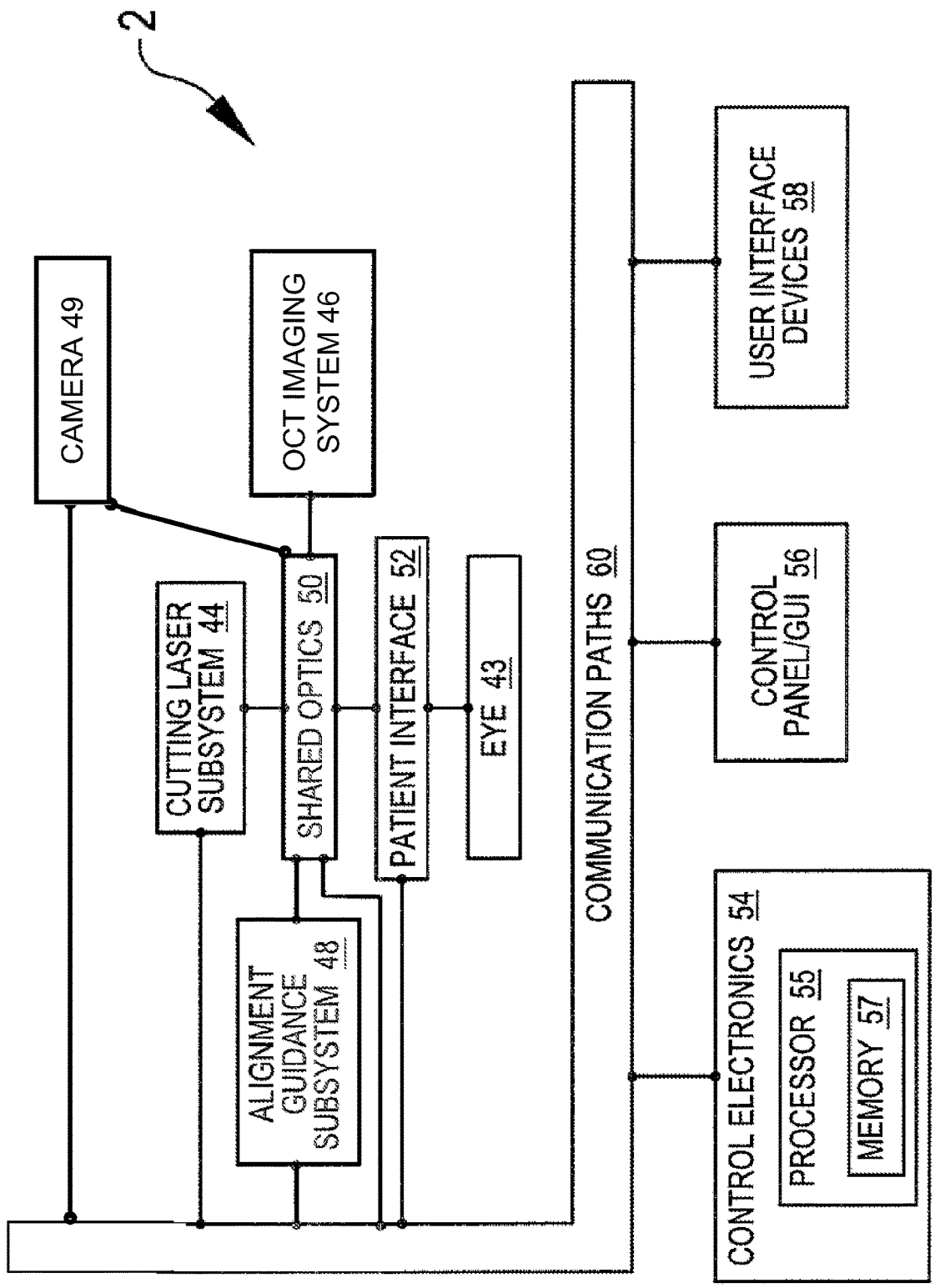
FIG. 2 is a simplified block diagram showing a top level view of the configuration of a laser eye surgery system having a patient interface in accordance with the present application.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a OCT imaging system 46, an alignment guidance system 48, a video camera 49, shared optics 50, a patient interface 52, control electronics 54, a control panel/GUI 56, user interface devices 58, and communication paths 60. The control electronics 54 are operatively coupled via the communication paths 60 with the cutting laser subsystem 44, the OCT imaging system 46, the alignment guidance subsystem 48, the video camera 49, the shared optics 50, the patient interface 52, the control panel/GUI 56, and the user interface devices 58.

In a preferred embodiment, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The OCT imaging system 46 is configured to measure the spatial disposition of eye structures in three dimensions. The measured eye structures can include the anterior and posterior surfaces of the cornea, the anterior and posterior portions of the lens capsule, the iris, and the limbus. In a preferred embodiment, the OCT imaging system 46 utilizes optical coherence tomography (OCT) imaging. As a non-limiting example, the system 2 can be configured to use an OCT imaging system employing wavelengths from 780 nm to 970 nm. For example, the OCT imaging system 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

There are many suitable possibilities for the configuration of the OCT imaging system. For example, alternative suitable configurations include time and frequency domain approaches, single and dual beam methods, swept source, etc., such as described in U.S. Pat. Nos. 5,748,898; 5,748,352; 5,459,570; 6,111,645; and 6,053,613.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the OCT imaging system 46, the alignment guidance subsystem 48, and the video camera 49. In a preferred embodiment, the shared optics 50 includes beam combiners to receive the emission from the respective subsystem (e.g., the cutting laser subsystem 44, and the alignment guidance subsystem 48) and redirect the emission along the common propagation path to the patient interface. In a preferred embodiment, the shared optics 50 includes an objective lens assembly that focuses each laser pulse into a focal point. In a preferred embodiment, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In a preferred embodiment, the scanning mechanisms are disposed between the laser diode and the objective lens such that the scanning mechanisms are used to scan the alignment laser beam produced by the laser diode. In contrast, In a preferred embodiment, the video system 49 is disposed between the scanning mechanisms and the objective lens such that the scanning mechanisms do not affect the image obtained by the video system.

The patient interface 52 is used to restrain the position of the patient's eye 43 relative to the system 2. In a preferred embodiment, the patient interface 52 employs a suction ring that is vacuum attached to the patient's eye 43. The suction ring is then coupled with the patient interface 52, for example, using vacuum to secure the suction ring to the patient interface 52. In a preferred embodiment, the patient interface 52 includes an optically transmissive structure (lens) having a posterior surface that is displaced vertically from the anterior surface of the patient's cornea and a region of a suitable liquid (e.g., a sterile buffered saline solution (BSS)) is disposed between and in contact with the posterior surface and the patient's cornea and forms part of a transmission path between the shared optics 50 and the patient's eye 43. The optically transmissive structure may comprise a lens 70 (see FIG. 3) having one or more curved surfaces. Alternatively, the patient interface 52 may comprise an optically transmissive structure having one or more substantially flat surfaces such as a parallel plate or wedge. In a preferred embodiment, the patient interface lens is disposable and can be replaced at any suitable interval, such as before each eye treatment.

The control electronics 54 controls the operation of and can receive input from the cutting laser subsystem 44, the OCT imaging system 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In a preferred embodiment, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Patient Interfaces

Figure 3:
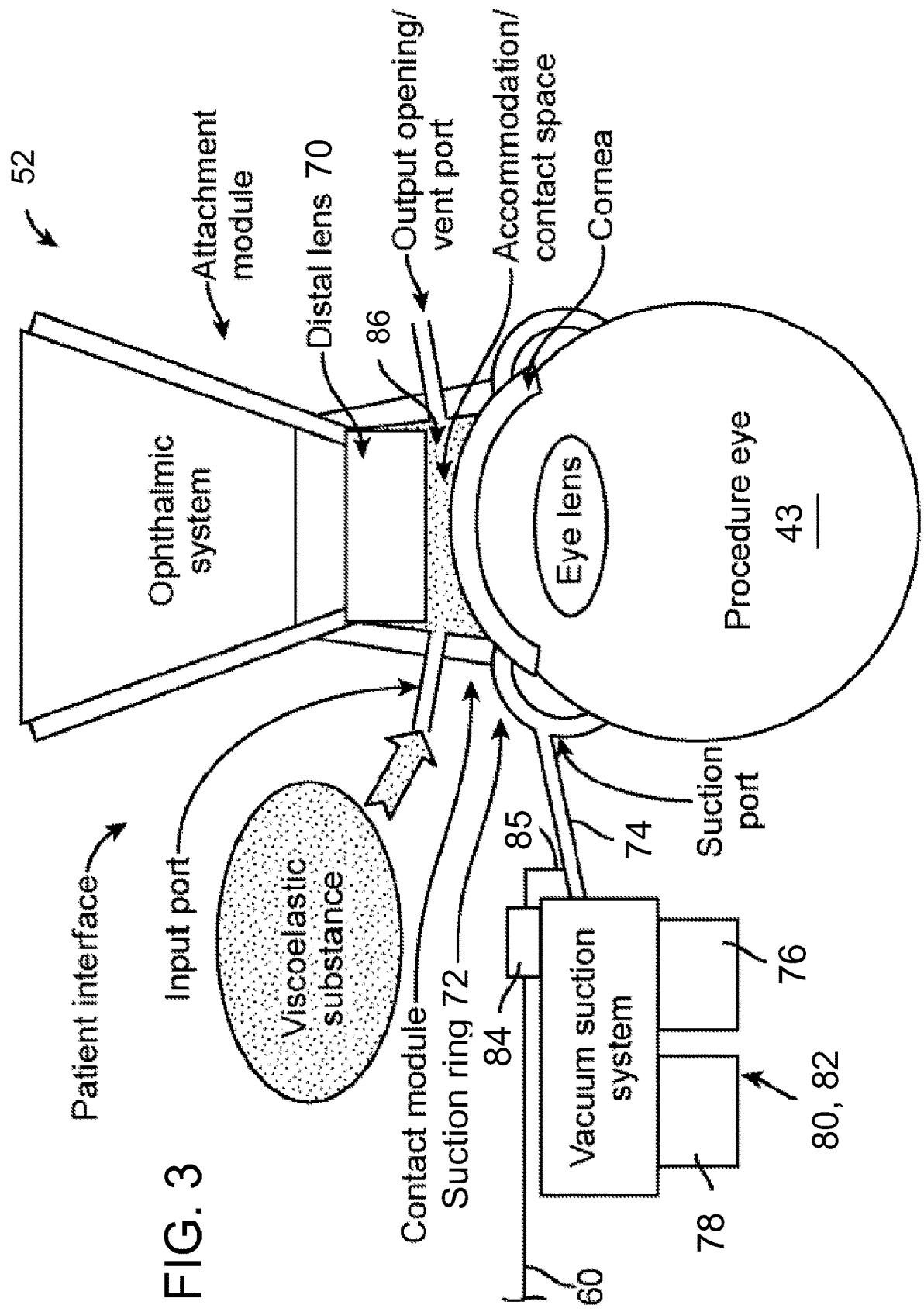
FIG. 3 is a sectional view of a patient interface used with the laser eye surgery systems described herein interposed between an ophthalmic intervention system and a patient's eye and depicting functional aspects thereof.

FIG. 3 depicts functional aspects of an exemplary patient interface used in the laser eye surgery systems described herein. As mentioned above, an exemplary patient interface assembly 52 incorporates a suction ring 72 coupled with the eye 43, for example, using vacuum. More specifically, a lower or distal end of the patient interface assembly 52 is placed in contact with the cornea of the eye 43 and suction drawn through a first suction line 74 coupled to the suction ring. The first suction line 74 extends from the suction ring 72 to a vacuum source, as will be described. A plurality of components is coupled to suction line 74, and may be coupled along first suction line 74 in series. A first fluid collector comprising a first container 76 is coupled to patient interface assembly 52 to receive fluid therefrom. The first fluid collector comprising first container 76 may comprise any one or more of many structures suitable to collect a liquid or viscous material as described herein. The fluid collection container 76 has an outlet to which is coupled a first fluid trap or stop 78. The first fluid stop 78 comprises a float valve 80 or a porous structure 82 to pass a gas such as air and inhibit flow of a liquid or viscous material as described herein, so as to stop substantially the flow of the liquid or viscous. A coupling sensor 84 can be coupled to the suction ring 72 and the first line 74 upstream of the porous structure 82 by a fluid line 85, for example. The coupling sensor 84 is coupled to the control electronics via the communication paths 60. As mentioned above, the patient interface assembly 52 includes an optically transmissive lens 70 with a posterior surface that is spaced vertically from the anterior surface of the patient's cornea across a region of a suitable liquid within a transmissive chamber 86.

Figure 4:
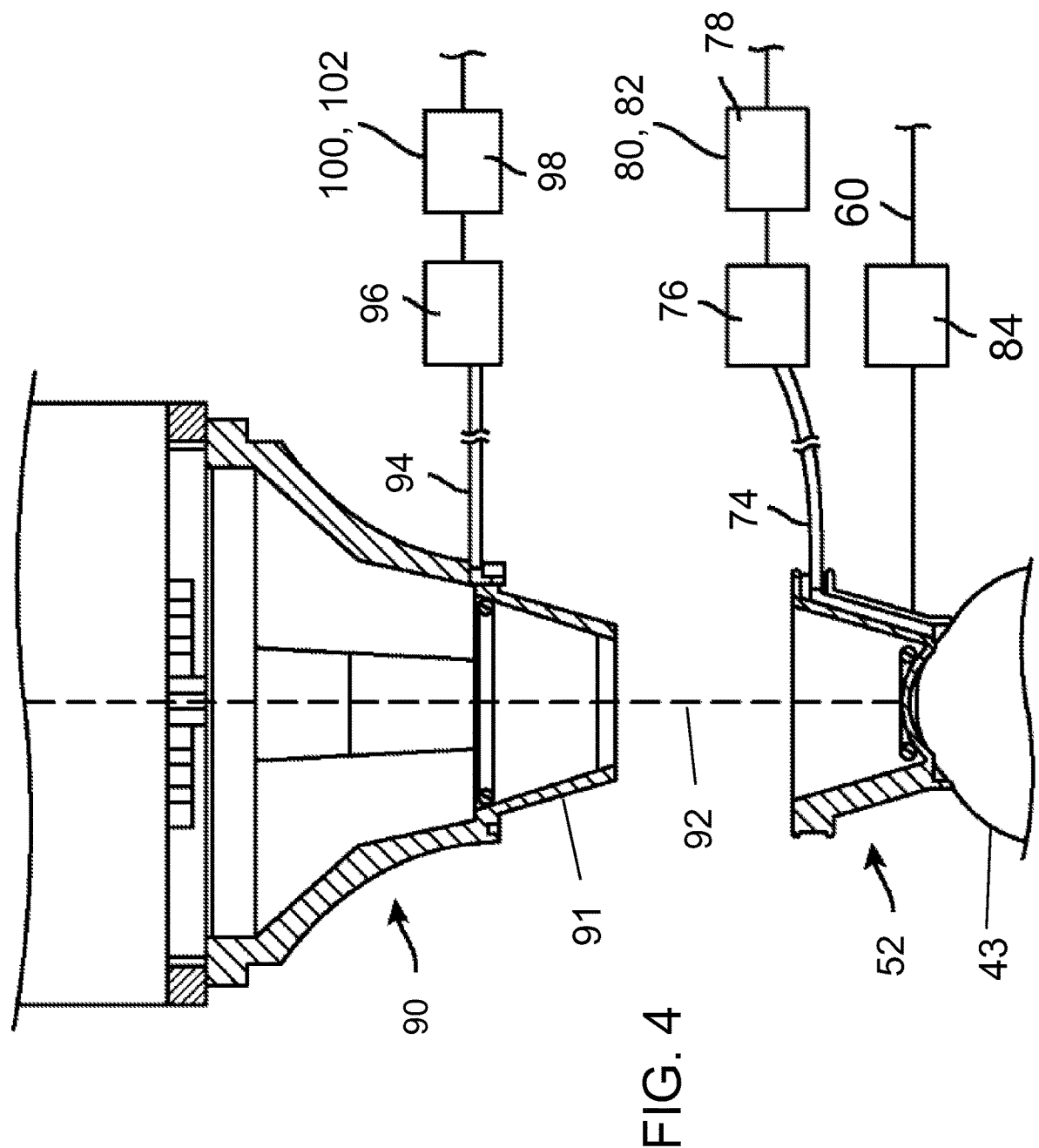
FIG. 4 is an exploded cross-sectional view of a two-piece patient interface used in the exemplary laser eye surgery system and ancillary components for applying and controlling section thereto, shown schematically.

FIG. 4 is an exploded cross-sectional view of a patient interface assembly 52 below a docking structure 90 comprising a docking cone 91. The patient interface assembly 52 is oriented about an axis 92 substantially aligned with an axis of the laser system and an axis of the eye 43. The axis 92 extends through an inner channel of docking structure 90 and an inner channel of the patient interface assembly 52, and the axis 92 can be substantially concentric with respect to both of these structures. The patient interface assembly 52 and the docking structure 90 may comprise components of the patient interface assembly, and these structures may be separable so as to define separate components of the patient interface assembly 52. Alternatively, the patient interface assembly 52 and the docking structure 90 can be provided together as a substantially inseparable component of the patient interface assembly 52. The docking structure 90 couples to a receptacle of the laser system 2 and to the patient interface assembly 52.

Patient Interface Suction Systems

Schematic elements of the suction system for the patient interface assembly 52 are also shown in FIG. 4. The fluid collector 76 and fluid stop 78 can be coupled to the suction line 74 which, in turn, couples to the suction ring placed on the eye. The first suction line 74 couples to the fluid collector comprising container 76 and porous structure 82 as described herein. The coupling sensor 84 couples to the suction ring and the first line 74 upstream of the porous structure 82 as described herein, for example. The coupling sensor 84 is coupled to the control electronics with the communication path 60 as described herein. A second suction line 94 to vacuum clamp the docking structure 90 to the patient interface 52 includes a container 96 and fluid stop 98 and any one or more of many structures suitable to collect a liquid or viscous material as described herein. For example, the second fluid collector 96 includes a porous structure 100 or float valve 102 as described herein.

Figure 5:
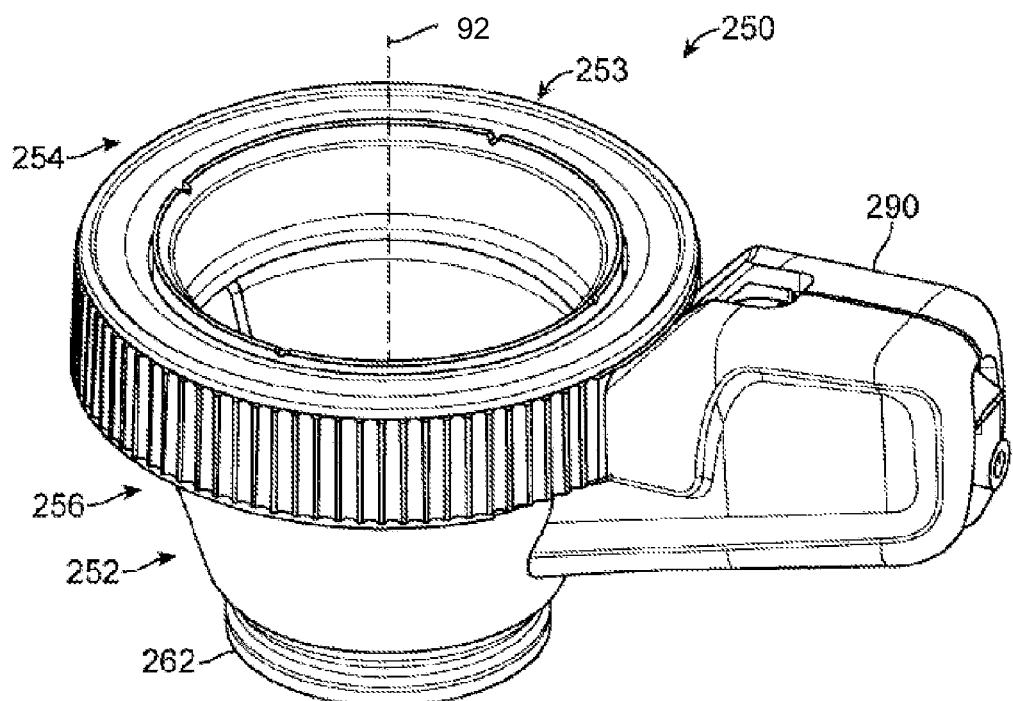
FIGS. 5 and 6 show a perspective view and a cross sectional view, respectively, of a two-piece patient interface used in the exemplary laser eye surgery system.
Figure 6:
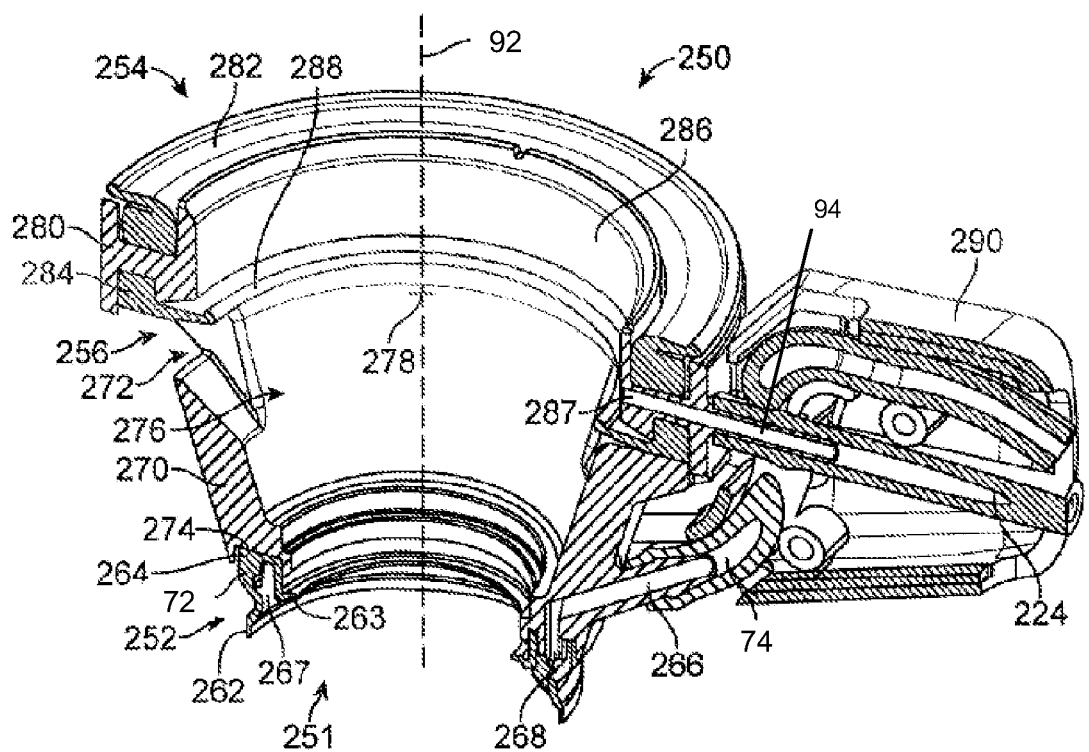

FIGS. 5 and 6 show details, in perspective and cross-sectional views, respectively, of a patient interface assembly 52 used in the exemplary laser eye surgery system. Certain aspects of the suction systems described above will be given like numerals for consistency between the drawings. Patient interface assembly 52 comprises opening 251 on a posterior end portion 252 dimensioned to receive the cornea of eye 43. The posterior end portion 252 may comprise an elastic suction ring 72. The patient interface assembly 52 comprises an anterior end portion 254 and an intermediate portion 256 extending between the posterior end portion 252 and the anterior end portion 254. The posterior end portion 252, the anterior end portion 254, and the intermediate section 256 are located about the axis 92 for alignment with an axis of the eye, and for alignment with an optical axis of system 2, so as to align optical axis of system 2 with the eye 43. The patient interface assembly 52 may comprise a handle 290.

The first suction line 74 (see FIGS. 3 and 4) can be coupled to the interior of the suction ring 72 with a channel 266 and an annular channel 268 extending substantially around an anterior portion of suction ring 72 interior.

The suction ring 72 comprises an elastomeric component comprising medical grade silicon, for example. The suction ring 72 may comprise an outer rim 262 and an inner rim 263. The inner rim 263 and the outer rim 262 can be dimensioned so as to fit on a peripheral portion of cornea and may engage a portion of the conjunctiva of the eye over the sclera of the eye, for example. The inner and outer rim are located at different locations along axis 92 such that outer rim 262 comprises a posterior end of patient interface assembly 52, and inner rim 263 is located anterior to the outer rim. The angle extending between outer rim 262 and inner rim 263 may correspond to an angle of the eye, so as to engage the eye and fix the eye with suction ring 72. The inner rim 263 and outer rim 262 preferably comprise sealing blades to form a seal with the eye and enable a vacuum clamp thereto. The suction ring 72 may comprise a support bolster 267 to inhibit tissue movement between the inner rim 263 and the outer rim 262 upon application of suction.

The intermediate section 256 includes a stiff housing 270 to couple the eye to the docking structure 90. A channel 272 can be formed in housing 270 to allow placement of fluid into the transmissive chamber 86 (see FIG. 3) and release of fluid from chamber 86 so as to inhibit pressure increases therein. The housing 270 defines an annular channel 274 formed in a posterior surface of the housing to receive the annular suction ring 72. The housing 270 may comprise a passage defined with an inner surface 276. The inner surface of housing 270 forms a conical surface, such as a frustum of a cone for example. The docking structure 90 comprising the optically transmissive lens 70 (see FIG. 4) can position a posterior surface of the lens at location 278 along the axis 92. The volume of transmissive chamber 86 can be determined based on the dimensions of inner surface 278, the position of posterior surface of lens 70 along axis 92 and the approximate location of the cornea along axis 92. The approximate location of cornea along axis 92 preferably corresponds to the location of channel 274 which receives the suction ring. A substantial portion of the transmissive chamber 86 can be defined with stiff housing 270 such that chamber 86 comprises a substantially constant volume. The housing 270 is desirably formed of a rigid material to add stiffness to the housing, for example a suitable plastic material.

The anterior end portion 254 comprises an annular structure 280 including an annular groove that receives a gasket 282 to engaging the docking structure 90. The annular structure 280 extends substantially around anterior end portion 254 and comprises a portion of housing 270. The annular structure 280 may comprise an opening 287 to couple to second line 94, as well as an inner annular surface 286 dimensioned so as to guide the docking structure 90 toward an annular seal 284. The annular gasket 284 desirably features an inner rim 288 to contact the docking structure 90 and form a seal. The gasket 282 is spaced apart from gasket 284, such that suction of second line 94 forms a vacuum clamp.

Figure 7:
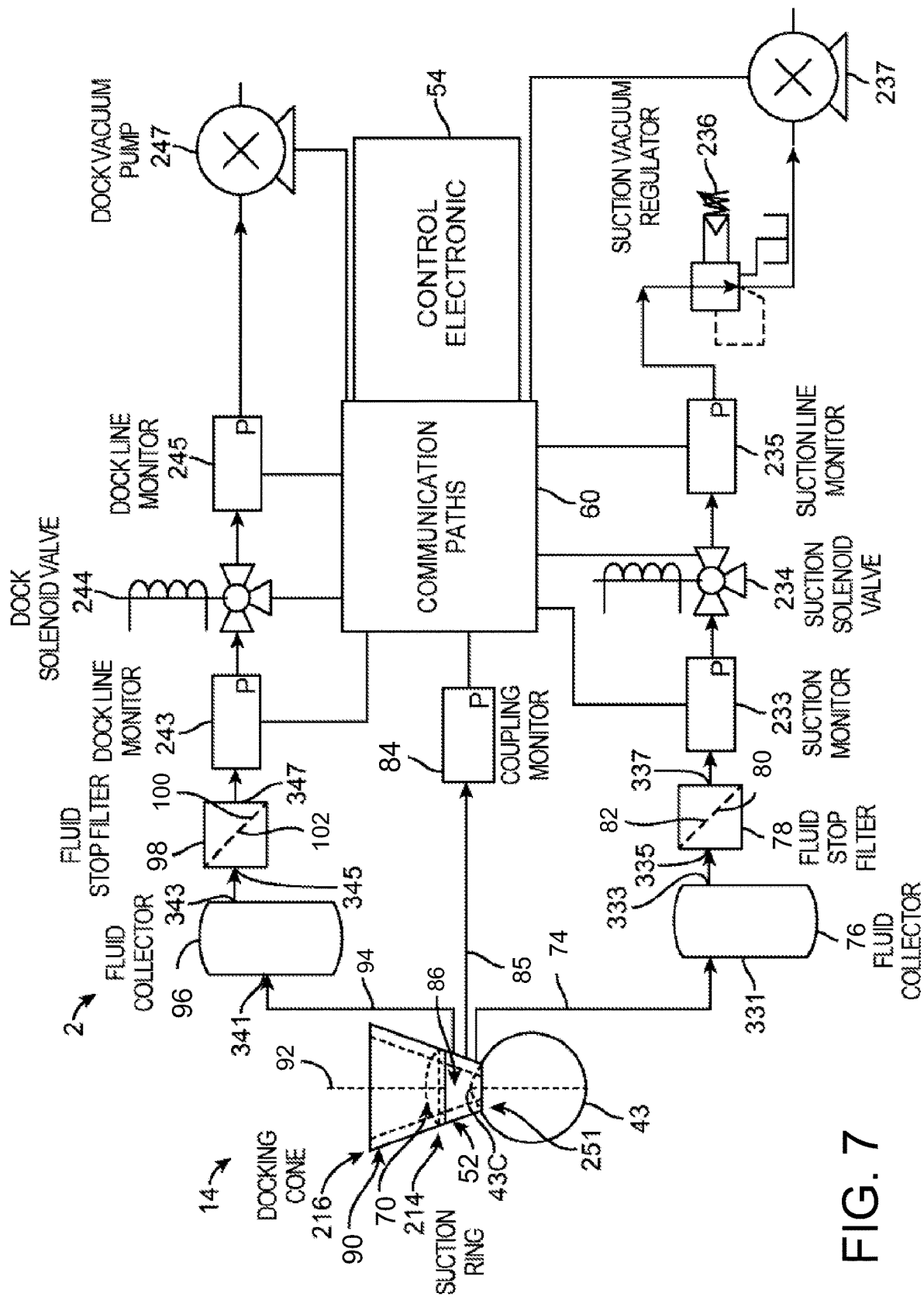
FIG. 7 shows a schematic diagram of support subsystems for the patient interface of the laser eye surgery system.

FIG. 7 shows a more comprehensive schematic diagram of support subsystems for the patient interface 52 of the laser eye surgery system 2. For context, FIG. 7 illustrates the eye 43, the laser system 2, and the patient interface assembly including the docking structure 90 and patient interface 52. The docking structure 90 is desirably conical between the anterior end portion 216 and the posterior end portion 214, and further houses the transmissive lens 70. The lens 70 can be located on the docking structure 90 or the patient interface assembly 52, or combinations thereof. The posterior surface of the lens 70, along with the inner surface of the patient interface 52 defines the interface fluid chamber 86 when placed on the eye.

The patient interface assembly 52 couples to one or more suction lines to retain the eye 43 when the cornea 43C extends into opening 251; for example the first suction line 74 and second suction line 94. The first suction line 74 extends from the suction ring 72 (see FIG. 3) to a vacuum source such as an eye retention structure vacuum pump 237. As mentioned, the suction line 74 couples the first fluid collector 76 to patient interface assembly 52 to receive fluid therefrom. The first fluid collector 76 comprises an inlet 331 and an outlet 333. The first fluid stop 78 couples to outlet 333 of first container 76 and includes the float valve 80 or porous structure 82 to pass a gas such as air and inhibit flow of a liquid or viscous material so as to stop substantially the flow of the liquid or viscous. The first fluid stop 78 comprises an inlet 335 and an outlet 337. The inlet 335 is coupled to the outlet 333 of the container 76.

The outlet 337 of the fluid stop 78 is coupled to a suction monitor 233, which can be positioned along first suction line 74 in order to monitor suction of the line. Desirably, suction monitor 233 comprises a pressure sensor positioned along the suction line downstream of the porous structure 82 and preferably between the fluid stop 78 and a solenoid valve 234. The pressure sensor 233 is coupled to control electronics 54 via one or more communication paths 60, as described herein. The pressure sensor 233 includes one or more transducers responsive to pressure of suction line 74. The suction solenoid valve 234 can be coupled to control electronics 54 via the communication paths 60. The first suction line 74 may further include a suction line monitor 235 between suction solenoid valve 234 and a suction vacuum regulator 236 to monitor suction downstream of suction solenoid valve 234. The suction vacuum regulator 236 can be provided along first suction line 74 so as to provide a regulated amount of pressure to eye 43 with the suction ring, for example suction pressure between about 300 and 500 mm Hg (millimeters Mercury), for example. The outlet of the suction vacuum regulator 236 is coupled to an inlet of the eye retention structure vacuum pump 237. The eye retention vacuum pump 237 is also coupled to control electronics 54 with communication paths 60.

The components along first suction line 74 facilitate coupling of the patient interface assembly 52 to the eye 43. Preferably, the first container 76 comprises a volume that is greater than a volume of the transmissive fluid chamber 86 of patient interface. When used to couple to the eye, patient interface assembly 52 can be placed on eye 43 with the liquid or viscous material within chamber 86, and suction applied to patient interface assembly 52. If the patient interface assembly 52 is not sufficiently coupled to eye 43, the fluid of chamber 86 is drawn into container 76 with suction. After a particular amount of the liquid or viscous material is drawn into container 76, a portion passes through outlet 333 and onto porous structure 82 so as to inhibit flow of fluid through the porous structure. If the first fluid stop 78 comprises the float valve 80, a portion of the liquid or viscous material passes through outlet 333 and triggers the float valve 80 to close so as to inhibit flow of fluid through the first fluid stop 78. The volume of the container 76 greater than the volume of chamber 86 allows the physician to place substantial amounts of fluid within the chamber when coupling the patient interface assembly 52 to the eye. For example, the volume of the container 76 comprises at least about twice the volume of the chamber 76, so that the user of system 2 has at least about two attempts to couple patient interface assembly 52 to eye 43 before the flow of suction 222 is substantially inhibited by fluid stop 78. In a preferred embodiment, the chamber 86 comprises a volume of about 0.5 to 2 cubic centimeters (hereinafter "cc") and container 76 comprises a volume within a range from about 1 to about 4 cc, for example.

Desirably, the ratio of container 76 volume to chamber 86 is limited such that the suction of line 74 can engage eye 2 with sufficient suction pressure in a sufficiently short amount of time, so that the retention structure can be readily used by a physician. For example, the volume of container 76 comprises no more than about twenty times the volume of chamber 86, and more preferably no more than about five times the volume of chamber 86.

A coupling sensor 84 can be coupled to patient interface assembly 52, for example with the fluid line 85 seen in FIG. 3, in order to monitor coupling of patient interface assembly 52 to eye 43. Coupling sensor 84 comprises a force transducer or a pressure transducer, for example. Preferably, fluid line 85 couples to the suction ring 72 of patient interface assembly 52 upstream of the fluid stop 78 such that coupling sensor 84 can rapidly measure changes in suction pressure and issue a warning to the user or interrupt the laser, for example, when an amount of pressure in line 85 rises above a threshold amount. Coupling of fluid line 85 upstream of fluid stop 78 can provide a more rapid response to changes in suction pressure than suction monitor 233 located downstream of fluid stop 78. The coupling sensor 84 can be coupled to electronic control 54 with communication paths 60 and the output of coupling sensor 84 can be used to control operation of laser system 2.

The second suction line 94 extends from the patient interface assembly 52 to a vacuum source such as dock vacuum pump 247. The second suction line 94 provides suction to an interface between the docking structure 90 and patient interface assembly 52, so as to clamp the docking structure to the patient interface assembly. Suction line 94 extends between patient interface assembly 52 and second fluid collector 96. Dock vacuum pump 247 couples to the anterior end portion 254 of patient interface assembly 52 via suction line 94 so as to engage the docking structure 90. Second container 96 comprises an inlet 341 and an outlet 343 to which the second fluid stop 98 is coupled. The second porous structure 100 or second float valve 102 inhibits flow of a liquid or viscous material as described herein, so as to stop substantially the flow thereof. The second fluid stop 98 comprises an inlet 345 coupled to the outlet 343 of the second container 96 and an inlet 345. The outlet 347 couples to a dock monitor 243, which can be positioned along second suction line 94 in order to monitor suction for coupling docking structure 90 to patient interface assembly 52. Suction monitor 243 comprising a pressure sensor is positioned along the second suction line downstream of the second porous structure 100 or second float valve 102 between the fluid second stop 98 and a second solenoid vale 244. The pressure sensor 243 can be coupled to control electronics 54 via the communication paths 60, as described herein. The pressure sensor 243 preferably comprises a transducer responsive to pressure of the suction line 94. The suction solenoid valve 244 is coupled to control electronics 54, and the second suction line 94 may include a suction line monitor 245 to monitor suction downstream of suction solenoid valve 244. The suction line monitor 245 preferably couples to an inlet of the vacuum pump 247, which is also connected to the control electronics 54.

The second fluid collector 96 preferably comprises a volume less than first container 76. The second fluid collector 96 desirably collects substantially less fluid than the first fluid collector, as the first line 74 may often couple to patient interface assembly 52 at a location below second line 94. Decreasing the volume of the second container 96 may provide more rapid suction clamping of the docking structure 90 to the patient interface assembly 52. Alternatively, the container 96 may comprise a volume that is greater than container 76.

The coupling lines as described herein may comprise lines for fluidic coupling known to a person of ordinary skill in the art and may comprise one or more of tubing, flexible tubing, rigid tubing, plastic tubing, metal tubing or manifolds, for example. The containers as described herein may comprise similar materials and can be constructed by a person of ordinary skill in the art based on the teachings provided herein.

Figure 8A:
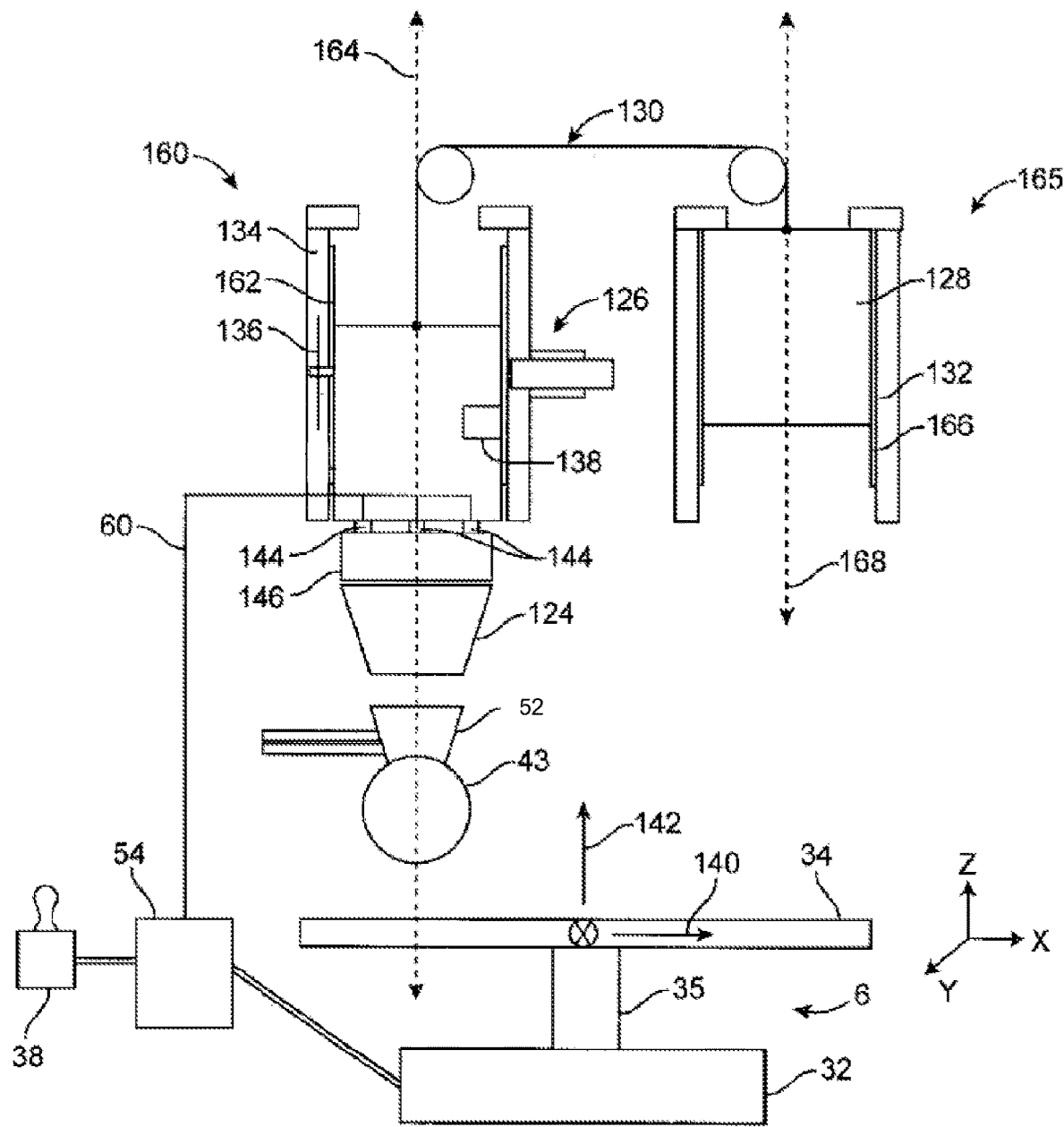
FIGS. 8A and 8B schematically illustrate exemplary components and steps for securing the patient's eye relative to the patient interface.
Figure 8B:
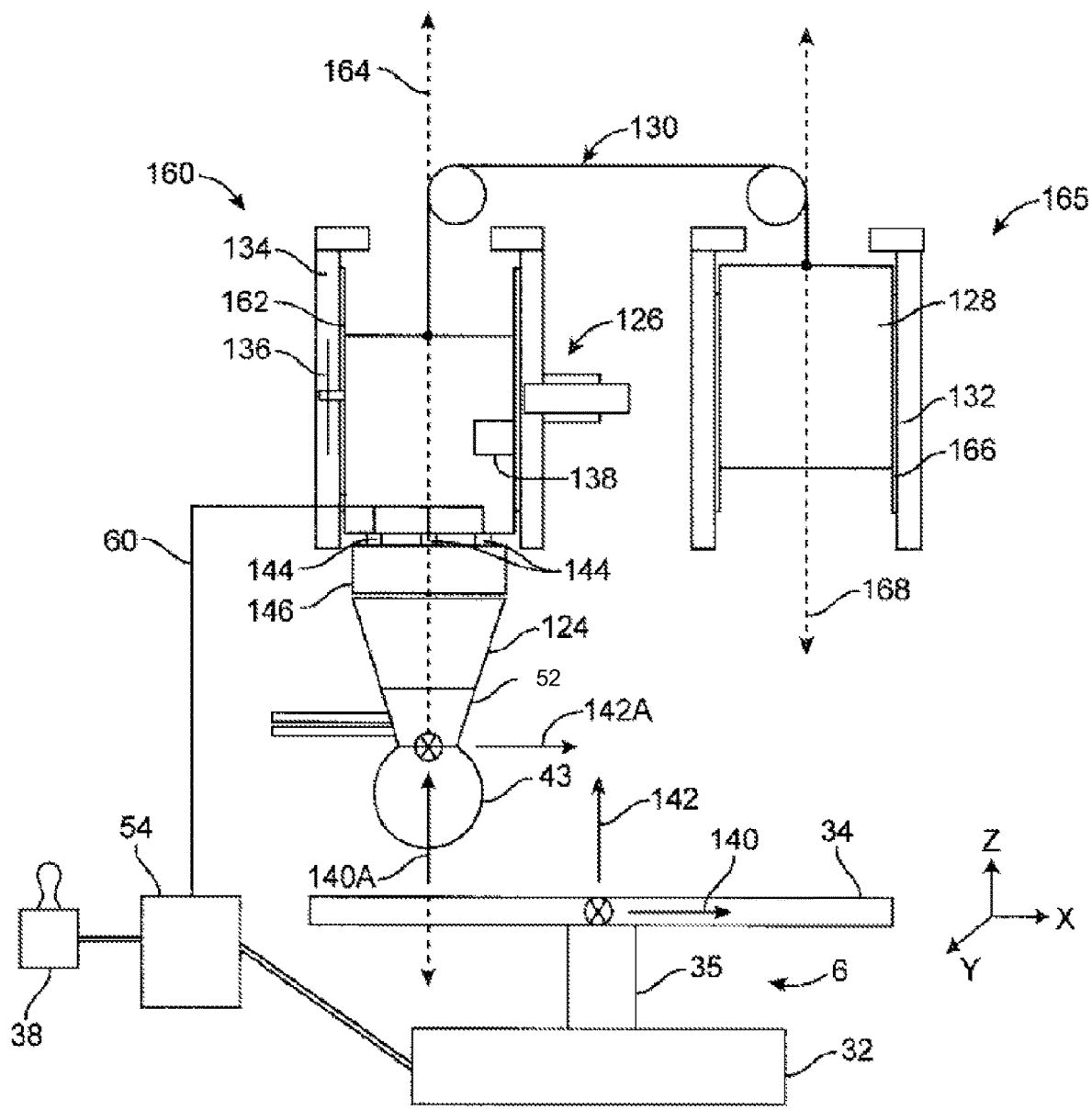

FIGS. 8A and 8B schematically illustrate exemplary components and steps for securing the patient's eye relative to the patient interface. FIG. 8A shows a preliminary step of coupling the patient's eye 43 with a patient interface 52. The patient will typically be resting on a top side of the patient support bed 34, which as shown by arrow 140 can be moved laterally in both the X and Y directions as well as vertically in the Z direction as shown by arrow 142. As mentioned above, the patient interface 52 may comprise an annular vacuum ring to couple to the eye with suction and a second vacuum line to apply suction to a lens placed over the eye.

The patient interface 52 may comprise a component of a patient interface assembly 160. The patient interface assembly 160 may comprise the housing 134, the patient interface 52, and a counterweight 128, for example. The patient interface assembly may also include a guide 162, for example a guide formed with a channel in the housing, so as to allow movement of the patient interface along an axis 164, typically a vertical axis. Such vertical movement is facilitated by a counterweight 128 which is housed within 132 and coupled to the patient interface 52 via cable assembly 130. The counterweight 128 may comprise a component of a counterweight assembly 165 including the housing 132 and a second guide 166 so as to allow movement of the counterweight 128 along an axis 168, typically a vertical axis. The housing 134 of the patient interface assembly 160 also comprises a linear encoder 136 to determine the vertical position of the housing assembly 52. The housing 134 further comprises a locking mechanism 126 which can be actuated to lock the patient interface 52 at a desired vertical position. In many embodiments, the counterweight 128 biases the patient interface 52 to be at this desired vertical position. When the patient interface 52 is at the desired vertical position, the locking mechanism 126 can lock into receptacle 138 in the patient interface 52. The locking mechanism 126 may comprise one or more of a detent, a lock and key mechanism, an opening to receive a linear protrusion, or a rotating cam, a flat surface to receive a friction brake. The friction brake may be configured to break free from the flat surface if the vertical force from the patient interface 52 surpasses a threshold limit that would be considered dangerous to the patient.

The patient interface 52 comprises a disposable lens cone 124 (equivalent to the docking structure 90 described above) which is configured to couple to the patient interface 52. The disposable lens cone 124 couples to the main body of the patient interface 52 via coupling adapter 146. As shown in FIG. 8B, once the patient interface 52 is coupled to the patient's eye 43, the patient interface 52 can be coupled to the disposable lens cone 124 to couple the patient's eye 43 to the interface assembly 52. Because the patient is resting on and secured to the patient support bed 34, the position of the patient's eye 43 can be varied laterally in the X and Y directions as shown by arrow 142A (FIG. 8B) as well as in the vertically in the Z direction as shown by arrow 140A by varying the position of the patient support bed 34 relative to the base 32, for example, by adjusting the patient chair joystick control 38 which adjusts a linkage 35 of the patient chair 6.

The patient interface assembly 160 comprises a plurality of force sensors or transducers 144 disposed between the main body of the patient interface 52 and the coupling adapter 146. Typically, the force transducers 144 will lie in the same horizontal plane normal to the vertical axis 164 of the patient interface 52 and parallel to the patient interface 52 and the disposable lens cone 124. The force transducers 144 detect the amount of vertical force between the main body of the patient interface 52 and the coupling adapter 146, including the force between the patient interface 52 and the patient's eye 43, when the suction cup 124 is coupled to both the patient's eye 43 and the disposable lens cone 124. The force sensors 144 signal when the patient moves around a lot after the system is stabilized. The force transducers 144 transmit data regarding measured force via communications paths 60 to the other subsystems of the laser eye surgery system 2 including the control electronics 54, the control panel/GUI 56, and the user interface devices 58.

The patient interface assembly 160 comprises at least three force transducers 144. The force transducers 144 measure forces in the Z-direction between the patient interface 52 and the patient's eye 43. Because there will typically be at least three force transducers 144, the force differential between the transducers can be used to calculate the magnitude and direction of the forces between the patient interface 52 and the patient's eye 43 in the X, Y, and Z directions. For example, the patient interface 52 may send the force data from the force transducers 144 to the control electronics 54 which in turn calculates the force between the patient interface 52 and the patient's eye 43 in the X, Y, and Z directions. The calculated patient interface-to-eye forces can be displayed and the laser eye surgery system operator can adjust the position of the patient support bed 36 via patient chair joystick control 38 so that the patient interface to eye forces remain constant over the course of a laser eye surgical procedure. For example, the laser surgery system operator can view the displayed forces and through the patient chair control input device 38, adjust the position of the patient support bed 36. In many embodiments, this procedure can be automated. For example, the control electronics 52 may calculate the patient interface to eye forces in the X, Y, and Z directions and automatically adjust the position of the patient support bed 36 accordingly as in method 900 described below.

The patient interface 52 can be moved vertically and locked in place at a desired position by actuating locking mechanism 126. The patient is seated onto the patient support bed 36 and the patient's eye 43 is coupled the patient interface 52 so that the patient interface 52 will typically be moved upward by moving the patient support bed 36 upward. When the linear encoder 136 detects that the patient interface 52 is in the desired vertical position, the linear encoder 136 will send a signal to the control electronics 52 to indicate that the patient interface 52 is in the desired vertical position. The locking mechanism 126 may then lock the patient interface 52 in the desired vertical position. The control electronics 54 may then limit or prevent further upward movement of the patient support bed 34 to prevent any injury to the patient's eye 34 that may occur if the patient support bed 34 is moved up while the patient interface 52 remains in place, which would otherwise sandwich the patient's eye 43. While the patient support bed 34 is limited or prevented from further upward movement, lateral movement of the patient support bed 34 will typically be unrestricted.

The patient interface 52 can be moved upward within the housing 134 beyond the position the patient interface 52 would be in if locked into position by locking mechanism 126, giving the patient interface 52 some vertical leeway within the housing 134 as the patient interface 52 is moved into the desired vertical position.

Detection of Vacuum Leak

A preferred laser cataract surgery using the aforementioned system is done by connecting the patient's eye with the laser system via a liquid-filled patient interface. The lower part of the patient interface attaches to the patient's eye by applying a vacuum over a ring-shaped area. The patient interface is then filled with a suitable sterile liquid (e.g., a sterile buffered saline solution (BSS)) interior to this ring, so that the sterile liquid is in direct contact with the patient's cornea. The patient is then moved with the chair to a position where the top part of the patient interface can be attached to an overhanging laser system by pulling vacuum over a second area, also with the shape of a ring. The sterile liquid is also in direct contact with the laser system's optics and the becomes part of the optical system of the instrument, interfacing the optical hardware with the patient's eye.

During treatment, the laser energy is transmitted into the patient's eye through the sterile liquid contained in the patient interface. Precise positioning of the laser beam in the human eye is very important and the system optics, interface liquid and eye media are taken into consideration by the system software.

If during treatment, the vacuum attachment of the interface to the patient were to be lost, sterile liquid could be aspirated by the vacuum system. The sterile liquid would fill the vacuum conduits in a way that would preclude fast enough detection of the loss of vacuum. This situation could be caused by patient movement. If the sterile liquid were to be displaced by air, the laser would transmit differently because the air has a smaller index of refraction. In addition, the eye could move away relative to the system optics. This would be a particularly serious condition during the lens segmentation, because the effect of displacing the water by air increases the power of the system optics, so that the cutting of the lens segmentation pattern would occur in a more anterior location, closer to or even in the cornea.

When a typical vacuum loss event occurs, the patient's movement causes a leak in the vacuum seal between the stationary patient interface and the eye tissue. This compromised seal is what causes fluid to be displaced with atmospheric air.

The present application proposes a three-fold solution to detection of vacuum loss. First of all, a video feed of the eye is monitored during treatment so that an air bubble that indicates vacuum loss is detected before the treatment delivery location is changed by the new media (air vs sterile liquid). Secondly, the force sensors 144 (FIG. 8A) on the patient interface are monitored for early signs of patient unrest that are predictors of subsequent vacuum loss. And finally, vacuum sensors 84, 233, 235, 243, 245 (FIG. 7) are carefully monitored for transient changes that are also predictors of subsequent vacuum loss. The proposed solution includes using all of the above three monitoring activities in conjunction with a Bayesian algorithm that computes the probabilities of an imminent vacuum loss event given the current state of the force sensor, vacuum sensor and video.

Figure 9B:
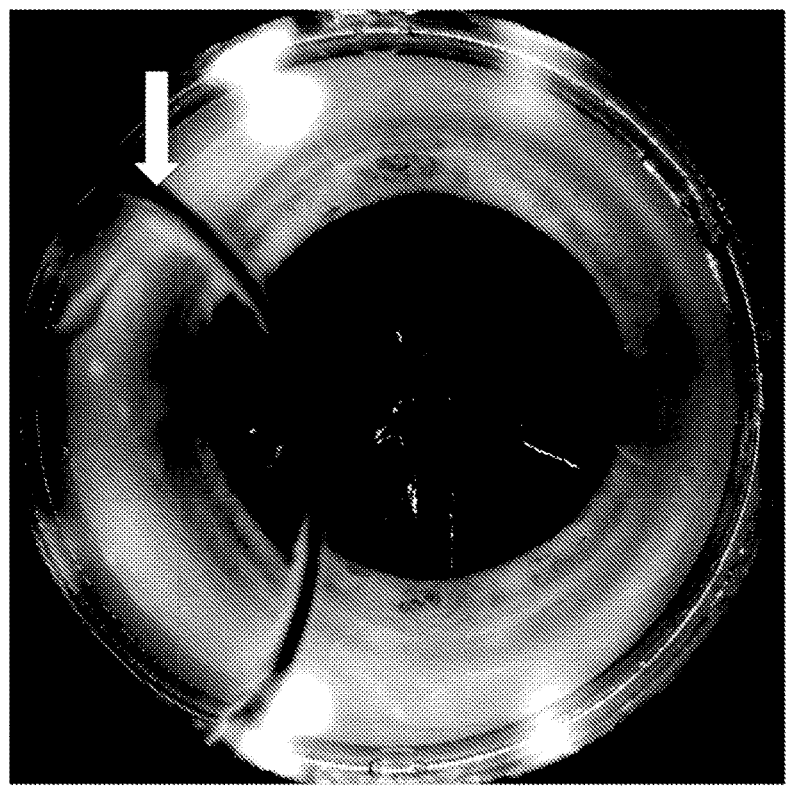
FIG. 9A is a video image of the eye with a perimeter of a suction ring divided into sectors, and FIG. 9B indicates a bubble edge as it crosses one of the sectors.
Figure 9A:
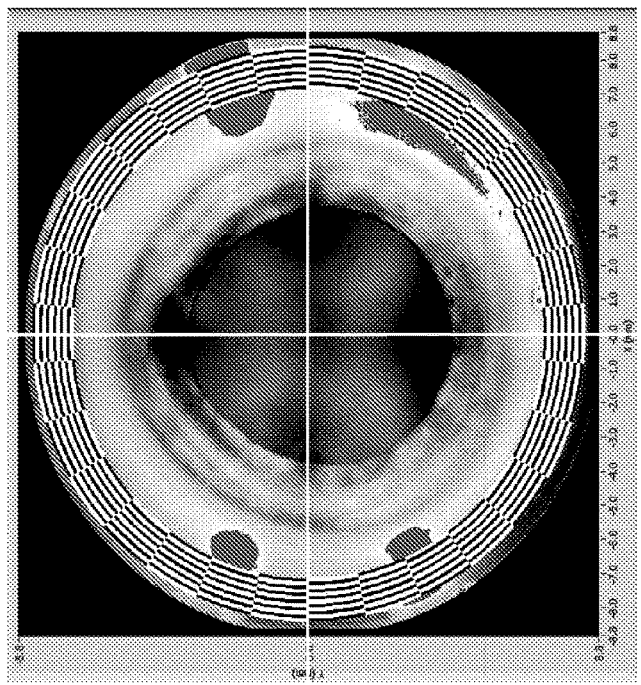

When the vacuum is lost and displaced by air, an air bubble is created on one of the sides of the patient interface and grows until it fills the entire space previously filled with water. FIG. 9A is a video image of the eye taken using the video camera 49 (FIG. 2) with a perimeter of a suction ring divided into sectors. When the vacuum seal between the eye and patient interface is compromised, the higher pressure air in the atmosphere drives into the patient interface, displacing the fluid. This action creates a bubble at the perimeter, which spreads throughout the fluid space between the disposable lens and the cornea. In the video image of FIG. 9B, a bubble edge indicated by a white arrow is detected as it crosses one of the sectors. By monitoring each sector for a change in pixel values, the formation of a vacuum leak bubble can be detected, and thus the laser can be stopped before the bubble spreads towards the center and interferes with the intended optical treatment delivery.

Figure 10:
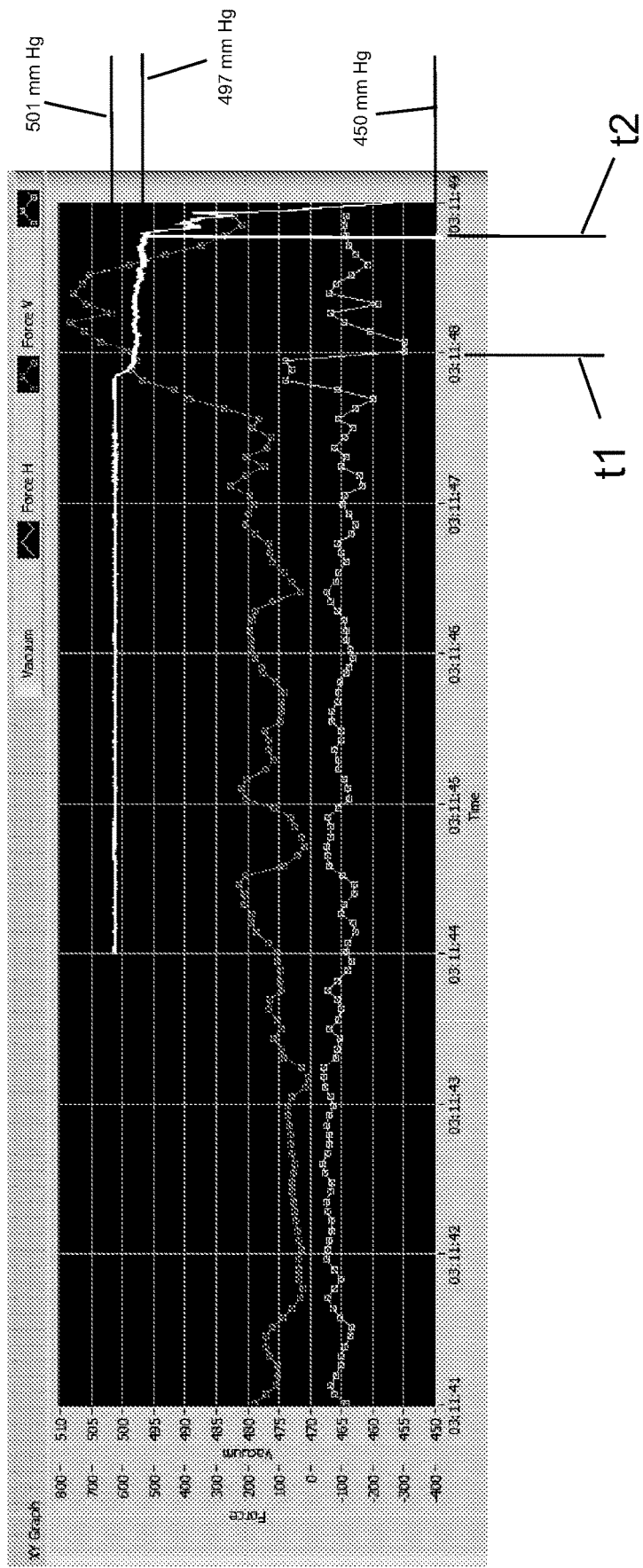
FIG. 10 is a plot depicting a signal from a vacuum sensor in a patient interface recorded during a suction loss event.

The plot of FIG. 10 depicts the vacuum sensor signal (see white trace) generated from data recorded when a suction loss event occurred with a patient on the laser system described herein. Shortly before t1 (3:11:48), a vacuum loss event occurred and the vacuum strength dropped from 501 mmHg to 497 mmHg, where it stayed for nearly a second until t2. Soon after t2, the vacuum strength dropped further to 450 mmHg, crossing the detection threshold and triggering an alarm that ordinarily stops the treatment and the laser emission. The sterile liquid displaced and aspired by the vacuum system occluded the vacuum conduit, preventing timely vacuum drop detection by delaying by close to a second (t2-t1). Since the sterile liquid has a higher viscosity than air, a column of water takes longer to go through the vacuum conduits. However, immediately prior to this vacuum sensor instability, the physical force sensors (red and green traces) detect perturbations greater than those seen when the vacuum is stable (here, from time 03:11:44 to 03:11:47).

The readings from the sensors (vacuum, pressure or force) 84, 144, 233, 235, 243, 245 (FIGS. 7 and 8B) can be monitored and analyzed to determine if a perturbation is sufficiently beyond a typical range of forces seen during treatment (e.g. forces due to the patient's heart rate or breathing rate). Since the sensors are unaffected by displaced fluid, their response time is as fast as the system and the algorithms used.

Additionally, although the aspirated fluid confounds a vacuum sensor's measurement, the data plot shows that the vacuum sensor still detects a subtle change from the normal steady vacuum profile. Thus, rather than rely solely on an absolute threshold of vacuum loss to stop the laser, the change in vacuum can serve as a metric with which to pause the treatment. As with the force sensors, analysis of the vacuum signal can be performed to determine if a change in vacuum is beyond that seen in a stable patient dock.

Using a Bayesian algorithm, the probabilities of an imminent vacuum loss event given the current state of the force sensor, vacuum sensor and video can be calculated. In a Bayesian approach, the various inputs or metrics that affect an outcome can be monitored, weighted and aggregated to produce a probability of an event. In this case, the three inputs of force sensor, vacuum sensor and video are simultaneously monitored and combined in an algorithm to predict whether a failure of vacuum is imminent, all in real-time and responsive in milliseconds. In a sample implementation of this approach, a program such as a LabVIEW code takes each measurement (force, vacuum, and video), and determines if the data trends suggest a suction break is likely to occur. If such conditions are met, a Boolean flag triggers a state change, which stops the laser and alerts the user that the dock integrity is compromised.

Alternatively, the monitoring and processing may provide information or a prediction that a particular disturbance is not sufficient to cause a failure, and the system should not be stopped. For instance, the level in one sensor or video feed may indicate a potential problem, while the other two are quiet. Also, the state in which the laser system operates also affects the output from the decision tree. For instance, a possible leak may be significant if the laser is in the process of cutting the lens of the eye, but not so much of a problem if the laser is making cuts in the cornea. In the latter case, what would normally trigger a leak warning will not halt the procedure.

It should be noted that if only one sensor, say the vacuum sensor, is monitored along with a stricter warning threshold, undesired false positive alarms may be triggered. For instance, when the vacuum sensor reads 497 mm Hg as in FIG. 10, a false positive alarm may be triggered, unnecessarily stopping treatments. The merit of combining information from all three sensors is specificity, that is, reduction of false positives, while increasing sensitivity, that is, capacity to detect events. Preferably at least two of the three sensors are monitored and their outputs combined, and there may be more than three inputs as well.

It should be understood that this approach using a Bayesian algorithm or its equivalent, or any of its three components, can be applied to any other ocular device that requires fixing a patient's eye steady for the duration of a procedure (e.g. other laser surgery systems that do not have any force or vacuum sensors can use the video detection method only).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting loss of vacuum in a patient interface of a laser eye surgery system having control electronics, comprising:
    docking a patient's eye to a suction ring of a patient interface which is aligned with an optical axis of the laser eye surgery system;
    supplying a sterile solution to a space within the patient interface between the patient's eye and a posterior surface of a transmissive lens held in the patient interface to form a transmissive chamber through which the laser eye surgery system may operate on the patient's eye;
    monitoring a video feed of the laser eye surgery through the patient interface to generate first data;
    monitoring a physical force sensor that detects movement of the patient's eye relative to the patient interface to generate second data, wherein the force sensor is disposed in the patient interface between a main body of the patient interface and a coupling adapter of the patient interface; and
    monitoring a vacuum sensor connected to a vacuum chamber of the suction ring to generate third data;
    aggregating data from all of the steps of monitoring with the control electronics and halting or delaying the laser eye surgery if at least two of the first data, second data and third data are consistent with a threshold likelihood of a significant vacuum leak.

2. The method of claim 1, wherein the step of aggregating is done using a Bayesian algorithm.

3. The method of claim 1, including monitoring the video feed of the laser eye surgery for the formation of a vacuum leak bubble.

4. The method of claim 3, wherein the video feed of the laser eye surgery is divided into sectors and the method includes monitoring each sector for a change in pixel values indicating the formation of a vacuum leak bubble.

5. The method of claim 1, wherein the physical force sensor detects movement of the patient's eye relative to the patient interface transverse to the optical axis.

6. The method of claim 1, wherein there are at least three force transducers that each sense the magnitude and direction of forces between the patient's eye and the patient interface, the method including sending data from the force transducers to the control electronics of the system and using a force differential between the transducers to calculate an aggregate force between the patient interface and the patient's eye in the X, Y, and Z directions.

7. The method of claim 1, wherein the vacuum sensor is fluidly connected to the vacuum chamber via a fluid line without any vacuum line components in between for rapid pressure response times.

8. The method of claim 7, further including a pressure sensor in the fluid line downstream of a point at which the vacuum sensor connects to the fluid line, wherein a fluid collector and a fluid stop are provided in the fluid line upstream of the pressure sensor, and wherein the method aggregates data output from the pressure sensor as well.

9. The method of claim 8, further including a second pressure sensor in a second fluid line fluidly connected to a second suction chamber between two components of the patient interface, wherein a fluid collector and a fluid stop are provided in the second fluid line upstream of the second pressure sensor, and wherein the method aggregates data output from the second pressure sensor as well.

10. The method of claim 1, wherein the control electronics of the laser eye surgery system monitors the progress of the surgery and, if the threshold is reached, determines whether the laser eye surgery should be halted or not depending on a current operating state.

* * * * *